(12) United States Patent
Ivany

(10) Patent No.: US 10,441,009 B1
(45) Date of Patent: Oct. 15, 2019

(54) FINGERTIP PROTECTORS

(71) Applicant: Cheryl A. Ivany, Dartmouth (CA)

(72) Inventor: Cheryl A. Ivany, Dartmouth (CA)

( * ) Notice: Subject to any disclaimer, the term of this patent is extended or adjusted under 35 U.S.C. 154(b) by 134 days.

(21) Appl. No.: 15/677,600

(22) Filed: Aug. 15, 2017

Related U.S. Application Data

(60) Provisional application No. 62/375,157, filed on Aug. 15, 2016.

(51) Int. Cl.
*A41D 13/08* (2006.01)
*A61F 13/10* (2006.01)
*A41D 19/015* (2006.01)
*A41D 13/05* (2006.01)

(52) U.S. Cl.
CPC ..... *A41D 13/087* (2013.01); *A41D 19/01529* (2013.01); *A61F 13/104* (2013.01); *A41D 19/01547* (2013.01)

(58) Field of Classification Search
CPC .......... A41D 13/087; A41D 13/08; A41D 19/01529; A61B 42/20; A61B 42/00; A61B 17/0493; A61F 13/105; A61F 2013/00395; A61F 2013/00404
See application file for complete search history.

(56) References Cited

U.S. PATENT DOCUMENTS

| | | | | |
|---|---|---|---|---|
| 3,263,681 | A * | 8/1966 | Nechtow | A61B 42/20 2/21 |
| 4,751,747 | A * | 6/1988 | Banks | A41D 19/01529 2/161.8 |
| 4,908,881 | A * | 3/1990 | Field | A41D 13/087 2/163 |
| 5,879,771 | A * | 3/1999 | Kypreos | A41D 13/087 132/73.5 |
| D494,369 | S | 8/2004 | McDevitt et al. | |
| 7,249,385 | B2 | 7/2007 | Schukraft | |
| 2009/0013441 | A1 * | 1/2009 | Duffy | A41D 13/087 2/21 |
| 2012/0210486 | A1 * | 8/2012 | McJunkin | A41D 13/087 2/69 |
| 2014/0137306 | A1 * | 5/2014 | Nagda | A41D 13/087 2/21 |

\* cited by examiner

*Primary Examiner* — Robert H Muromoto, Jr.
(74) *Attorney, Agent, or Firm* — Cramer Patent & Design, PLLC; Aaron R. Cramer

(57) ABSTRACT

A fingertip protector having a flexible cover with a top contacting surface and a bottom gripping surface. A lip is attached to the flexible cover so as to define the contacting surface and a strap is attached on both of its ends to the flexible cover. The contacting surface is sized and shaped to fit on a tip of a finger and the strap is configured to wrap around a finger to assist in securing the contacting surface on the tip of the finger. The flexible cover is comprised of a heat-resistant elastomer. The contacting surface contacts the tip of a finger while the lip engages that tip to assist maintaining the finger and thumb tip protector in place.

9 Claims, 5 Drawing Sheets

FINGERTIP PROTECTORS

RELATED APPLICATIONS

The present invention is a continuation-in-part of, was first described in and claims the benefit of U.S. Provisional Application No. 62/375,157 filed Jul. 11, 2016, the entire disclosures of which are incorporated herein by reference.

FIELD OF THE INVENTION

The presently disclosed subject matter is directed to personal safety and protection devices. More particularly, the present invention relates to finger protectors for protecting the tips of fingers from pain due to contact with a hot surface.

BACKGROUND OF THE INVENTION

Personal hairstyles are available in thousands of different looks. A person's hairstyle can be as unique as one's personality and can be readily changed to fit a person's mood and lifestyle. However, achieving a desired look not necessarily easy.

In the world of hair styling, there are numerous tools that are used to achieve a desired look. One (1) very popular tool used in hair styling is the curling iron. A curling iron uses heat to add style, body, flips, flair, and the like to one's hair quickly and with a minimum of fuss. However, since a curling iron depends on heat to work it has an exposed heated area across its circumference and along its length. While this exposed heating surface enables it to heat and curl hair easily and quickly it also enables it to burn fingertips or thumb tips that are being used to style the hair.

In the prior art, one (1) approach to protecting fingertips and thumb tips from the heated areas of curling iron is to have the stylist wear heat-resistant gloves. While highly successful at protecting fingertips and thumb tips from heat such heat-resistant gloves can significantly reduce a wearer's dexterity, potentially resulting in a less than pleasing hairstyle while making the desired hairstyle far more difficult to achieve.

Accordingly, there exists a need for a protective device by which fingertips and thumb tips can be protected from burns while using curling irons, other heated hair care appliances, or other heated devices. Preferably such a protective device would be easy to use and would not reduce the dexterity of a wearer's fingers and thumb.

SUMMARY OF THE INVENTION

The principles of the present invention provide for a protective device by which fingertips and thumb tips can be protected from burns while using curling irons, other heated hair care appliances or other heated devices. Such a protective device does not significantly reduce a wearer's dexterity, it is effective, lightweight, and can be made available at low cost.

A fingertip protector that is in accord with the principles of the present invention includes a flexible cover having a top contacting surface and a gripping surface, a lip that is attached to the flexible cover so as to define the contacting surface, and a strap that is attached on both of its ends to the flexible cover. The contacting surface is sized and shaped to fit on a tip of a finger and the strap is configured to wrap around a finger to assist in securing the contacting surface on the tip of the finger.

In practice, the flexible cover is beneficially comprised of a heat resistant elastomer such as silicone rubber, polyurethane, polypropylene, polyesters, polyethylene terephthalate, polyethylene, polyvinyl chloride (PVC), latex or nylon. In any event the flexible cover should survive a brief contact with a hot device without passing sufficient heat to discomfort a wearer. In one (1) embodiment the flexible cover can survive a one second (1 sec.) contact with a surface at two hundred degrees Fahrenheit (200° F.) without notable damage and without transmitting sufficient heat to discomfort a wearer.

The flexible cover beneficially has a generally elliptical shape and is preferably generally flat. In addition, the strap is beneficially located near the center of the flexible cover. In practice, the strap extends around the nail of the finger to assist retaining the fingertip protector on a finger. To that end the strap forms an approximately "U"-shape that defines an open space that receives the distal phalanx of a finger. Preferably the strap creates a bias that helps retain the finger and thumb protector on a finger. Alternatively, or in addition the strap is comprised of the same material as the flexible cover.

Beneficially the contacting surface makes contact with the tip of a finger and even more beneficially approximates the shape of the tip of a finger. The lip may engage the tip of a finger so as to assist maintaining the finger and thumb tip protector in position on the finger.

The gripping surface may include alternating protruding ridges and grooves. If so the grooves may be formed between adjacent ridges. The grooves may be recessed and the ridges and grooves can run approximately parallel to each other. In practice, the ridges and grooves may be curved.

BRIEF DESCRIPTION OF THE DRAWING

The advantages and features of the present invention will become better understood with reference to the following more detailed description and claims taken in conjunction with the accompanying drawing, in which like elements are identified with like symbols, and in which:

DESCRIPTIVE KEY

Figure 1:
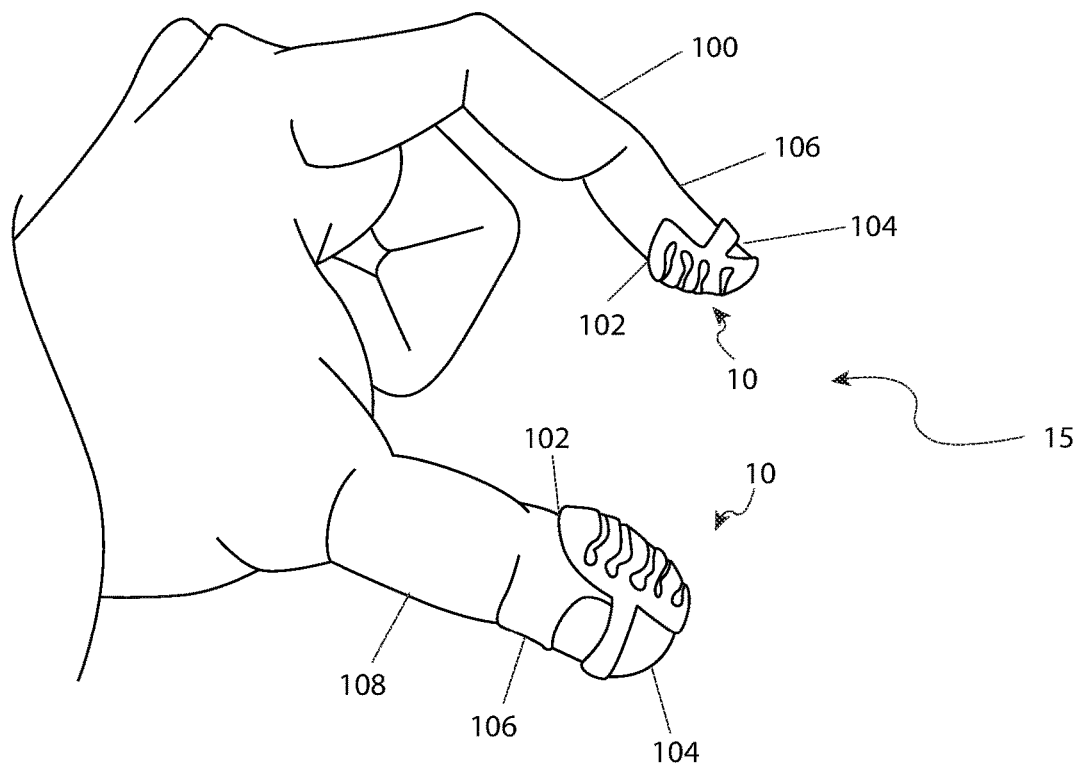
FIG. 1 is a side perspective view of a pair of finger and thumb tip protective devices that are in accord with a preferred embodiment of the present invention.

10 finger and thumb tip protector
15 device pair
20 flexible cover
22 strap
28 open space
30 contacting surface
32 lip
36 gripping surface
38 ridge
40 groove
100 finger
102 tip 104 nail
106 distal phalanx
108 thumb

DETAILED DESCRIPTION OF THE PREFERRED EMBODIMENT

The preferred embodiment of the present invention is depicted in FIGS. 1 through 5. However, the invention is not limited to the specifically described embodiment. A person skilled in the art will appreciate that many other embodiments of the invention are possible without deviating from the basic concept of the invention. Any such work around will also fall under the scope of this invention.

In the figures like numbers refer to like elements throughout. Additionally, the terms "a" and "an" as used herein do not denote a limitation of quantity, but rather denote the presence of at least one (1) of the referenced items.

The present invention is a finger and thumb tip protector 10 that provides a heat-resistant, flexible cover that protects the tip 102 of a wearer's finger 100 or thumb 108 from a hot surface while enabling full finger and thumb dexterity.

FIG. 1 presents an environmental side perspective view of two (2) finger and thumb tip protectors 10, which are generically referred to herein as a device pair 15. The individual finger and thumb tip protectors 10 are shown as being worn on the index finger 100 and on the thumb 108 of a wearer (e.g., a user). The finger and thumb tip protectors 10 are designed to easily slip on and off the distal end of the finger 100 and thumb 108. As shown in FIG. 1 the device pair 15 can work together to protect the index finger 100 and the thumb 108 as they perform tasks, particularly including when operating a heated tool or implement.

The device pair 15 enables a full range of motion of the finger 100 and thumb 108 so as to not restrict their dexterity. The device pair 15 is beneficially designed to protect the finger 100 and thumb 108 of a wearer when that wearer is operating a curling iron or other heated hair care appliance when styling one's own hair or when styling another's hair. The finger and thumb tip protectors 10 enable the wearer to handle and touch the hot surfaces of a hair care appliance without burns to the tips 102 of their finger 100 and/or thumb 108. However, it should be clearly understood that the finger and thumb tip protectors 10 can be used while performing other tasks using other implements while providing the full benefit of fingertip protection.

While FIG. 1 shows the device pair 15 on the index finger 100 and the thumb 108, a finger and thumb tip protectors 10 may be worn on other fingers 100 as well. A finger and thumb tip protectors 10 can be made in various sizes to accommodate different sized fingers 100, whether those sizes relate to being an index finger, a middle finger, a ring finger, a thumb or a little finger, or the fingers of different people. The finger and thumb tip protector 10 also can be made in various shapes to accommodate different fingers 100. It should be understood that the term "finger" as used herein may refer to the thumb, the index finger, the middle finger, the ring finger, and the little finger.

Figure 2:
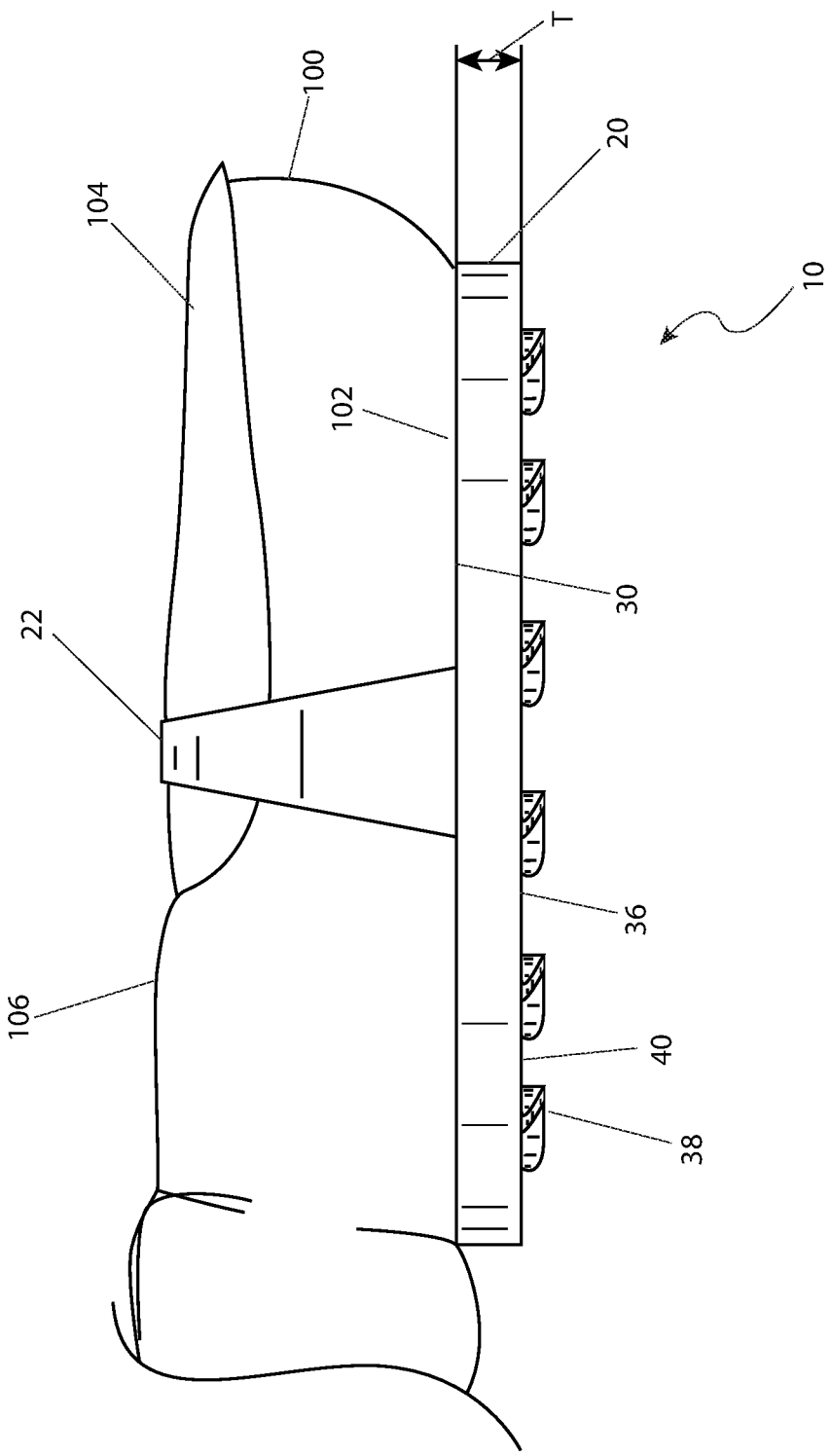
FIG. 2 is a side elevation view of the finger and thumb tip protective device shown in FIG. 1.

FIG. 2 presents an environmental side elevation view of a finger and thumb tip protector 10 worn on a finger 100. The finger and thumb tip protector 10 should be selected to be sized and shaped to cover a portion of the distal phalanx 106 of the finger 100 such as the tip 102 of the finger 100. In another embodiment, the finger and thumb tip protector 10 may be sized and shaped to cover the entire tip 102 of the finger 100.

The finger and thumb tip protector 10 is a one-piece member molded from a flexible, compliant and heat-resistant elastomer such as silicone rubber, polyurethane, polypropylene, polyesters, polyethylene terephthalate, polyethylene, polyvinyl chloride (PVC), latex or nylon. By heat-resistant it is meant that the heat-resistant elastomer will survive at least a brief contact with a device such as a curling iron and will not readily transmit heat from that device to a wearer's fingertip. For example, a heat-resistant elastomer should be a thermal insulator which can survive at least a one second (1 sec.) contact with a surface at over two hundred degrees Fahrenheit (200° F.) without notable damage and without transmitting sufficient heat to discomfort a wearer.

Figure 3:
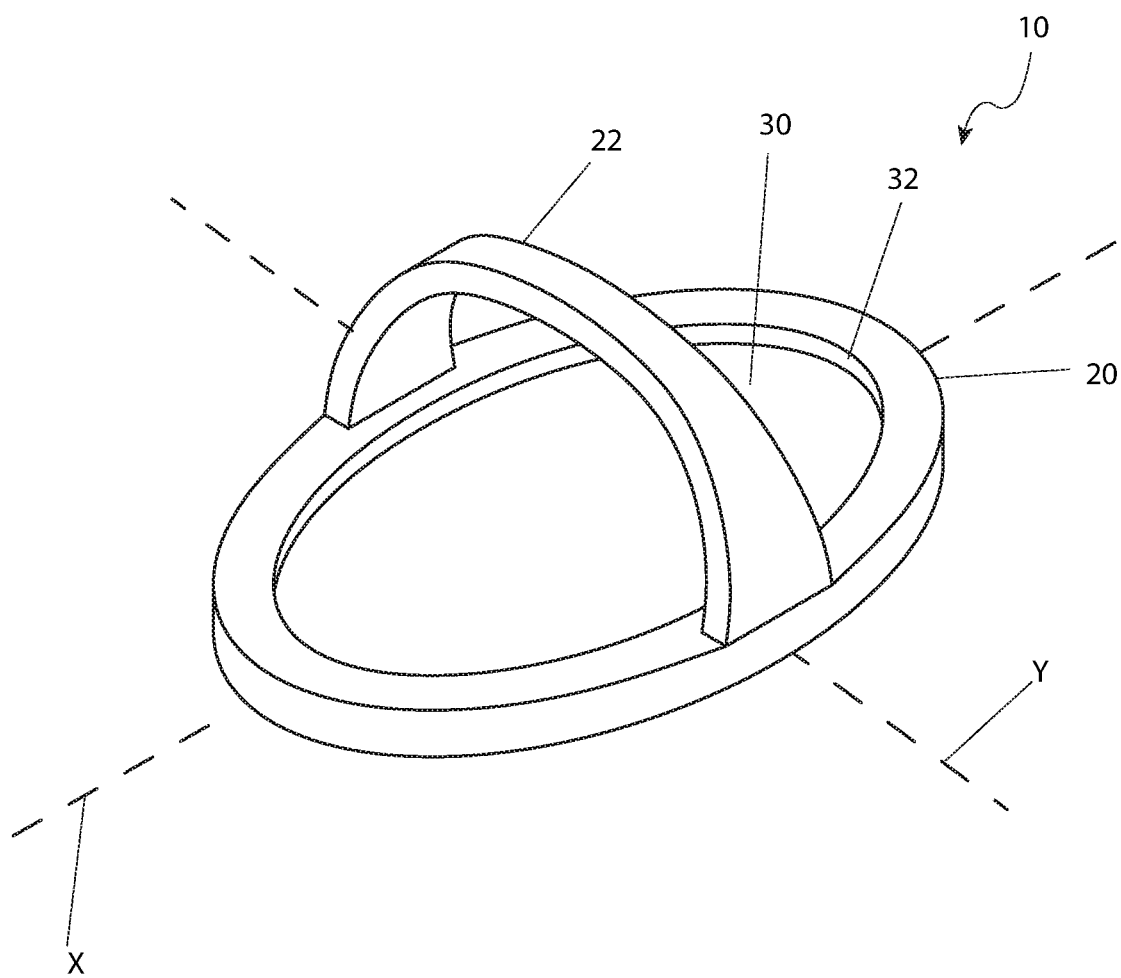
FIG. 3 is a side and top perspective view of the finger and thumb tip protective device shown in FIGS. 1 and 2.
Figure 4:
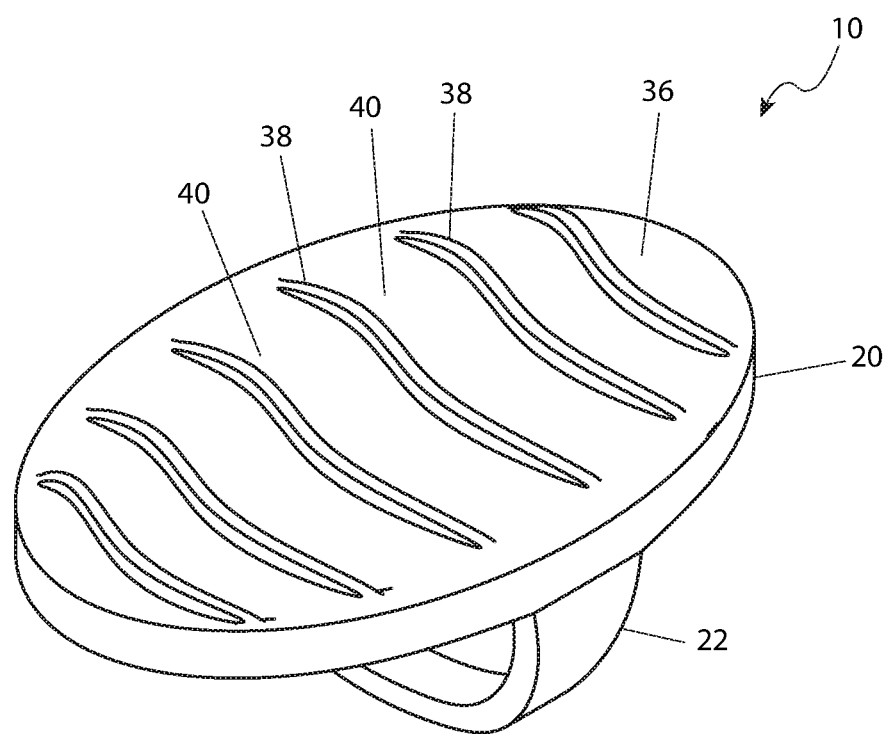
FIG. 4 is a side and bottom perspective view of the finger and thumb tip protective device shown in FIGS. 1-3; and, FIG. 5 is a front elevation view of the finger and thumb tip protective device shown in FIGS. 1-4.
Figure 5:
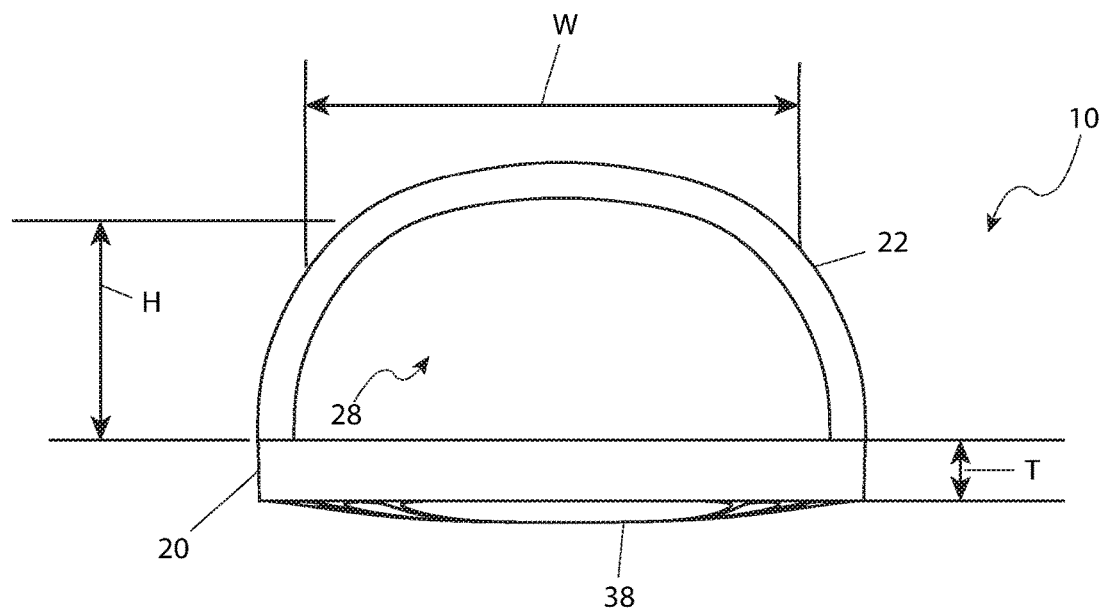

In addition to FIGS. 1 and 2, FIG. 3 illustrates a side and back perspective view, FIG. 4 illustrates a side and front perspective view, and FIG. 5 illustrates a front elevation view of the finger and thumb tip protector 10. The finger and thumb tip protector 10 includes a flexible cover 20 and a strap 22. As described in more detail subsequently the flexible cover 20 is configured to cover part of or the entire tip 102 of a finger 100. The strap 22 is configured to wrap around the finger 100 to secure the finger and thumb tip protector 10 to the distal phalanx 106 of the finger 100.

Referring now particularly to FIGS. 3-5, the flexible cover 20 has a generally elliptical shape which leans toward round or ovular such that it approximates the shape of the tip 102 of a finger 100. From the side, the flexible cover 20 is generally flat on both surfaces and has a relatively small thickness T. Referring now primarily to FIGS. 2 and 3, the flexible cover 20 is highly flexible such that it can conform to the profile of the tip 102 of a finger 100. By relatively small it is meant that the thickness T does not significantly impact on the flexibility of the flexible cover 20.

The strap 22 is beneficially located at about the center of the flexible cover 20. However, the strap 22 may be located at other locations on the flexible cover 20 to suit the particular finger and/or application. The strap 22 preferably extends around the nail 104 of the finger 100 on which the finger and thumb tip protector 10 is worn, ideally at or near the nail bed. The purpose of the strap 22 is to extend around a finger 100 to assist retaining the finger and thumb tip protector 10 on a finger 100. Referring now particularly to FIG. 5, the strap 22 has an approximately inverted "U"-shape body that defines an open space 28 that receives the distal phalanx 106 of the finger 100.

The strap 22 has a height H that ideally is slightly less than the height of the finger 100 and a width W that is slightly less than the width of the finger 100. The strap 22 is beneficial he made of the same elastic and resilient material as the flexible cover 20. The strap 22 should stretch to receive the finger 100 and should create a bias that helps retain the finger and thumb tip protector 10 upon the finger 100.

Referring now primarily to FIGS. 2 and 3, the flexible cover 20 forms a top contacting surface 30 that makes intimate contact with the tip 102 of the finger 100. In the example illustrated in FIG. 3 the contacting surface 30 is generally round, ovular or elliptical so as to approximate the shape of the tip 102 of the finger 100. Preferably the contacting surface 30 is recessed within the flexible cover 20 by a lip 32. That lip 32 ideally engages the tip 102 of a finger 100 so as to act as a ridge that assists maintaining the finger and thumb tip protector 10 in position on the finger 100.

Referring particularly to FIG. 4, the bottom of the flexible cover 20 forms a gripping surface 36. The gripping surface 36 may come into contact with a heated tool during use. The griping surface 36 has a surface texture that increases the friction of the finger and thumb tip protector 10.

As a specific example, the gripping surface 36 includes alternating protruding ridges 38 and grooves 40. Accordingly, the grooves 40 are formed between adjacent protruding ridges 38. In another example, the grooves 40 are recessed into the gripping surface 36. In that case the ridges 38 are formed by the portions of the gripping surface 36 disposed between adjacent recessed grooves 40. In any event the alternating ridges 38 and grooves 40 preferably run approximately parallel to each other. In another example, illustrated in FIG. 4, each of the ridges 38 and grooves 40 extends laterally across the gripping surface 36. Beneficially, and as illustrated in FIG. 4, the ridges 38 and grooves 40 are curved. As shown, each ridge 38 may include more than one (1) curve along the ridge 38.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated.

The invention claimed is:

1. A fingertip protector, comprising:
   a flexible cover having a top contacting surface and a gripping surface;
   a lip attached to the top of said flexible cover so as to define said contacting surface;
   a strap having a pair of ends, the pair of ends each attaches to said flexible cover;
   wherein said contacting surface is sized and shaped to fit on a tip of a finger; and,
   wherein said strap wraps around said finger to assist in securing said contacting surface on said tip of said finger;
   wherein said lip engages said tip of said finger so as to assist maintaining said finger and a thumb tip protector in position on said finger;
   wherein said strap extends around the nail of said finger to assist retaining said fingertip protector on said finger;
   wherein said strap forms a "U"-shape that defines an open space that receives said distal phalanx of said finger;
   wherein said strap creates a bias that helps retain said finger and thumb protector on said finger;
   wherein said flexible cover has a generally elliptical shape;
   wherein said contacting surface has the shape of the tip of said finger; and
   wherein said gripping surface includes a plurality of alternating protruding ridges and a plurality of grooves.

2. The fingertip protector according to claim 1, wherein said flexible cover is made of a heat-resistant elastomer selected from the group consisting of polypropylene, polyesters, polyethylene terephthalate, polyvinyl chloride, and nylon.

3. The fingertip protector according to claim 1, wherein said flexible cover survives a brief contact with a hot device without passing sufficient heat to discomfort a wearer.

4. The fingertip protector according to claim 1, wherein said flexible cover survives a 1 second contact with a surface at 200° F. without notable damage and without transmitting sufficient heat to discomfort a wearer.

5. The fingertip protector according to claim 1, wherein said strap is made of the same material as said flexible cover.

6. The fingertip protector according to claim 1, wherein said contacting surface makes contact with the tip of said finger.

7. The fingertip protector according to claim 1, wherein said grooves are formed between said alternating protruding ridges.

8. The fingertip protector according to claim 7, wherein said grooves are recessed.

9. The fingertip protector according to claim 1, wherein said alternating protruding ridges and said grooves run parallel to each other.

\* \* \* \* \*